United States Patent
Halpert

(10) Patent No.: US 10,959,803 B2
(45) Date of Patent: *Mar. 30, 2021

(54) MARKING DEVICE WITH METALLIC ELEMENT FOR USE IN X-RAY GUIDED SURGERY

(71) Applicant: Eli Halpert, West Hempstead, NY (US)

(72) Inventor: Eli Halpert, West Hempstead, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/965,002

(22) Filed: Apr. 27, 2018

(65) Prior Publication Data

US 2018/0243047 A1    Aug. 30, 2018

Related U.S. Application Data

(63) Continuation of application No. 15/157,108, filed on May 17, 2016, now Pat. No. 9,956,055.

(51) Int. Cl.
*A61B 90/00* (2016.01)
*B43K 29/08* (2006.01)

(52) U.S. Cl.
CPC .............. *A61B 90/39* (2016.02); *B43K 29/08* (2013.01); *A61B 2090/395* (2016.02); *A61B 2090/3908* (2016.02); *A61B 2090/3966* (2016.02); *A61B 2090/3983* (2016.02)

(58) Field of Classification Search
CPC . A61B 90/00; A61B 90/39; A61B 2090/3983; A61B 2090/395; A61B 2090/3966; A61B 6/12; A61B 6/547; G03B 42/00; G03B 42/02; G03B 42/047; A61N 2005/1051; H05G 1/28

USPC .................. 378/162, 163, 165, 204, 205
See application file for complete search history.

(56) References Cited

U.S. PATENT DOCUMENTS

| 5,897,264 | A | 4/1999 | Baudino |
| 6,299,373 | B1 | 10/2001 | Cheng |
| 2009/0253981 | A1 | 10/2009 | Hamilton et al. |
| 2011/0028836 | A1 | 2/2011 | Ranpura et al. |
| 2011/0097134 | A1* | 4/2011 | Allen ........................ B43K 7/00 401/23 |

FOREIGN PATENT DOCUMENTS

WO    2000/074565 A1    12/2000

OTHER PUBLICATIONS

International Search Report received for PCT Patent Application No. PCT/US2017/033135 dated Sep. 28, 2017, 5 pages.
Written Opinion received for PCT Patent Application No. PCT/US2017/033135 dated Sep. 28, 2017, 6 pages.
Supplementary European Search Report dated Jan. 16, 2020 from European Patent Appln. No. 17800103.8.

* cited by examiner

*Primary Examiner* — Jurie Yun
(74) *Attorney, Agent, or Firm* — Amster, Rothstein & Ebenstein LLP

(57) ABSTRACT

A disposable marker for use in preparation for medical procedures. The marker is made of plastic or such similar material that does not show up on an x-ray monitor. The marker includes one or more metallic elements that have an elongated aspect disposed in proximity to the marker tip. As such, a clinician may introduce the marker into an x-ray field and view it in space by following the metallic element an x-ray monitor.

11 Claims, 3 Drawing Sheets

MARKING DEVICE WITH METALLIC ELEMENT FOR USE IN X-RAY GUIDED SURGERY

FIELD OF THE INVENTION

The invention relates to the field of medical markers, more specifically to a marker having an integrated metallic element which allows the marker to be visible within an x-ray field.

BACKGROUND OF THE INVENTION

When performing x-ray guided surgery (such as certain vascular surgeries), a surgeon inserts a line into an artery or similar body site through a small incision in a patient's skin. Before making the incision, however, the doctor must locate an incision point and then mark it.

In order to locate and mark the incision spot—the following is done (in the current state of the art): A doctor places a metallic device, such as a clamp, into the x-ray field. Because metal shows up on an x-ray image, the doctor uses the metallic device to determine where in space the device is located in relation to the area of interest on the patient's x-ray image. The doctor watches the metallic device on the x-ray monitor and uses it to identify an external area that is appropriately positioned as an incision area. The doctor uses the metallic device to make a "dimple" in the skin and then removes the metallic device and marks the "dimple" with ink using an appropriate marking device.

There is a need in the art for a disposable marking device that is visible in an x-ray field—thereby allowing clinicians to locate an area and mark it with a single device.

SUMMARY OF THE INVENTION

The invention is a disposable marking device that has a metallic element embedded therewith. The combined marker and metallic element allows a doctor to view the marker on the x-ray monitor and then use it to make a mark on a patient's skin—dispensing with the need to first use a metallic device (like a clamp) for purposes of orientation.

The marker housing is made of plastic such as polypropylene, or any such similar material that does not obstruct the passage of x-rays. The metallic element embedded with the marker, on the other hand, does at least partially obstruct the passage of the x-rays, and as such, it is visible in an x-ray field. The inventive marker, thus, may be used to both locate a puncture area (by visualizing the metallic element in relation to a real time x-ray image) and to mark a puncture area (by pressing the marking tip on the selected puncture site).

DETAILED DESCRIPTION OF THE INVENTION

Embodiments of the present invention will now be described with reference to the above-identified Drawings. However, the Drawings and the description herein of the invention are not intended to limit the scope of the invention. It will be understood that various modifications of the present description of the invention are possible without departing from the spirit of the invention. Also, features described herein may be omitted, additional features may be included, and/or features described herein may be combined in a manner different from the specific combinations recited herein, all without departing from the spirit of the invention.

As described, in the process of x-ray guided surgery a surgeon needs to locate an area inside the human body for medical intervention purposes and then tag a corresponding site outside of the body for insertion of medical instruments/devices. For example, a surgeon may need to localize an artery of interest during cardiovascular surgery or he may need to identify an external area in which to insert screws or other orthopedic hardware with image guided assistance and localization.

Figure 1:
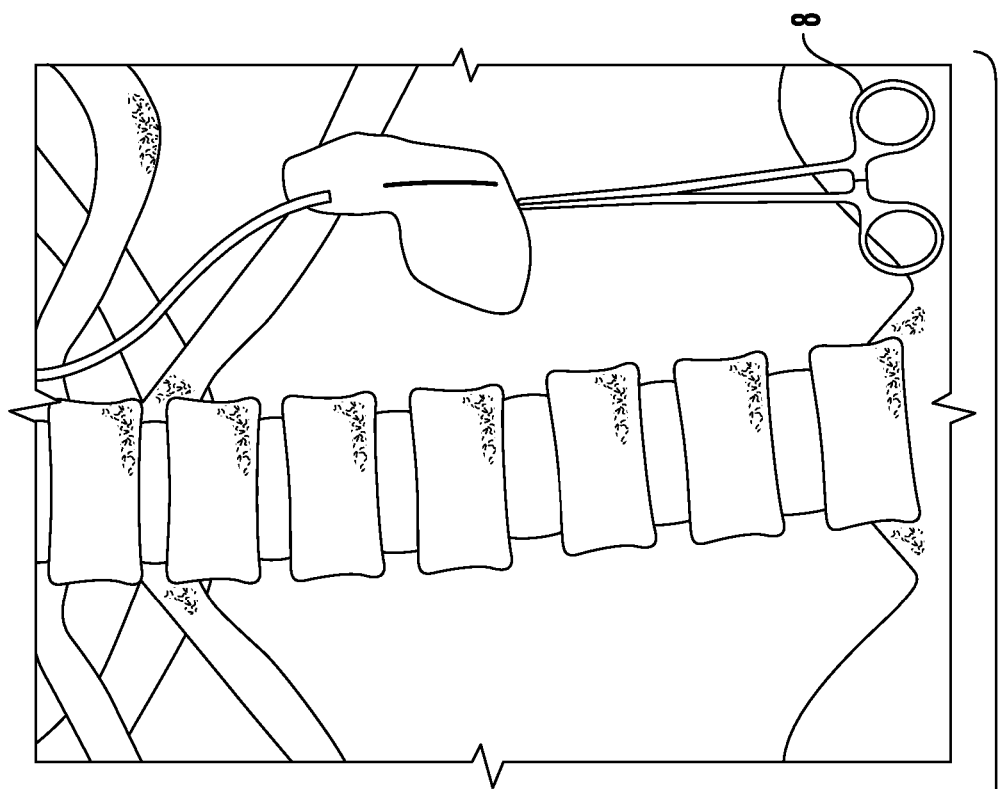
FIG. 1 is a schematic view of an x-ray field showing the prior art method of locating an incision spot.
Figure 1:
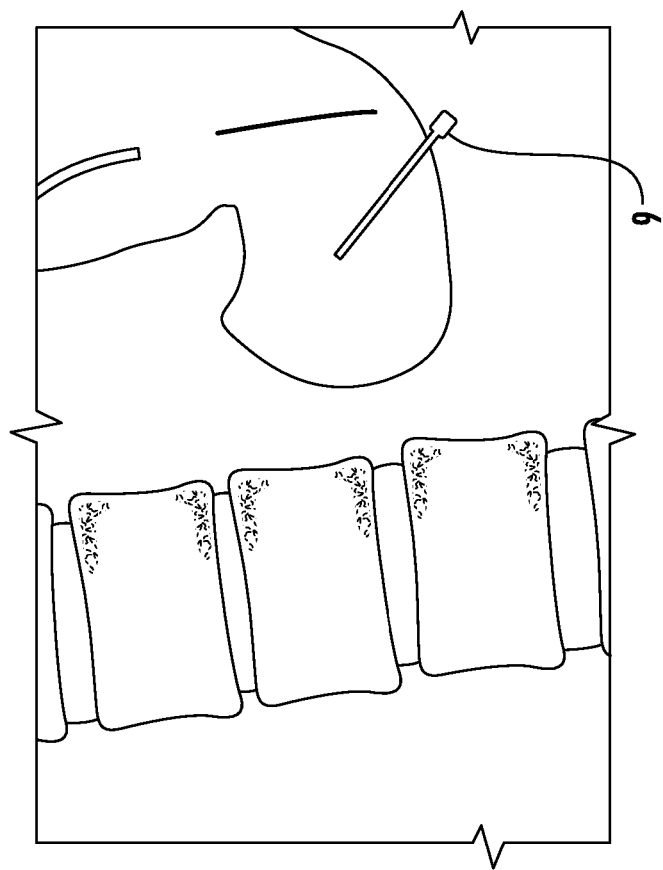

FIG. 1 shows a schematic view of the current method of identifying a location for incision/insertion. As shown, a metallic medical instrument such as a clamp 8 is brought into the x-ray field and it is placed at a selected area for insertion outside a patient's body. Having identified an external area for insertion—the clinician then uses a marking device to mark the identified location. As shown, subsequent to marking the spot, a medical instrument such as a needle or port 9 is inserted.

The invention set for the herein allows a physician to introduce a marking device into the x-ray field and visualize it in real time because of the metallic element embedded or contained therein. Once a desired location is identified, the surgeon need only mark the area using the same device. As such, rather than performing two steps of 1) placing a metallic device into the x-ray field and 2) removing the metallic device and marking the spot—the current invention allows physicians to use a single marker that achieves two purposes.

The inventive marking device is a felt marker or marking pen having an outer housing and an inner ink cartridge. The ink cartridge is a tubular core of absorbent material impregnated with ink that is surrounded by a plastic or such similar wrapping. The marker, thus, is relatively inexpensive and suitable for one-time use. A specialized metallic strip or radio-opaque indicia printed on the marker allows the marker to remain inexpensive—yet partially visible on an x-ray monitor.

In an embodiment of the invention, the marker housing is made of plastic such as polypropylene, or any such similar material that does not obstruct the passage of x-rays. The metallic element embedded with or otherwise attached to the marker, on the other hand, does obstruct the passage of the x-rays, and as such, it is visible in an x-ray field. In embodiments of the invention, the marking material such as ink is carried on a core of material that is absorptive to ink (or similar marking material) and it has a marking tip formed of porous, pressed fibers such as felt of the like. The marking tip, thus, allows for the transfer of ink to a patient's skin by lightly contacting the skin with the marking tip. The combination of a plastic marker and a specialized metallic element allows for an inexpensive marker that can be used to, both, locate a puncture site and mark the same, and that is suitable for single use.

Figure 2:
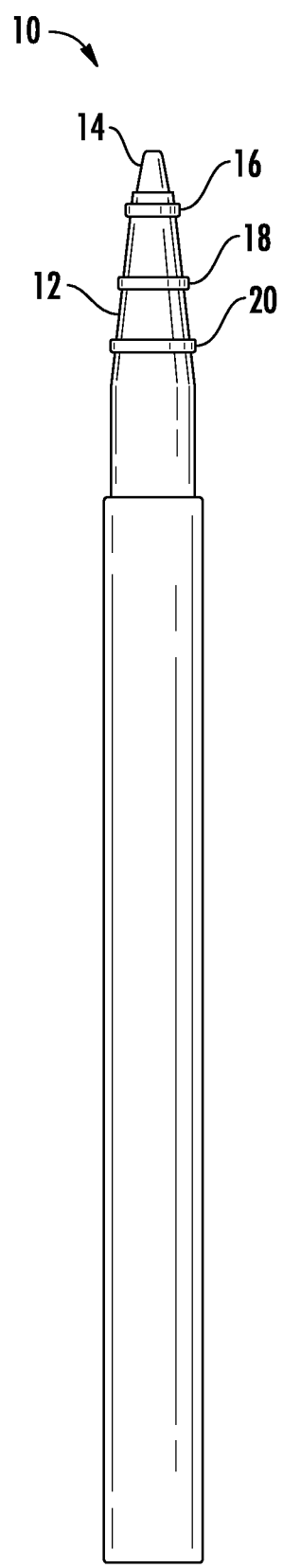
FIG. 2 shows a side view of a marker having a series of metallic rings in the proximity of its marking tip according to an embodiment of the invention.

FIG. 2 is a side view of a marking device according to an embodiment of the invention. As shown, marking device 10 has an outer casing or housing 12 similar to conventional markers. Housing 12 has an outer surface and an interior chamber which houses an ink cartridge. A marking tip 14 extending form the ink cartridge protrudes from housing 12.

In an embodiment of the invention one or more metallic rings are mounted to or embedded in the outer casing of the marker. FIG. 2 shows a plurality of metallic rings 16, 18, 20 mounted around the outer surface of the marker casing 12—in an area that is proximate to the marking tip 14. Metallic rings may be glued onto the marker 10 or embedded therein during manufacture. In use, the metallic rings 16, 18, 20 show up in an x-ray field and a doctor may, as such, move the marker 10 to a desired area with reference to the anatomical x-ray image. Once a desired location is found, the doctor need only press the marking tip 14 on the desired spot to make a mark thereon.

In a preferred embodiment of the invention, at least three metallic rings are provided around the distal tip of a marker—but more or fewer than three are within the teaching of the invention. The rings are preferably spaced apart and non-abutting. As such, the rings 16, 18, 20 in combination, have a longitudinal aspect which may be useful for the purpose of orientation. That is, a plurality of rings spaced over a segment of the marker allows a doctor to perceive the orientation of the marker in space.

Preferably rings 16, 18, 20 are placed on a sloping region of the marker (e.g. the sloping area bridging the marking tip and the remainder of the housing). As such rings are required to have three different sizes. That is, as shown, ring 18 is larger than ring 16 because it is positioned on an area of the marker having a larger diameter than the position of ring 16—and the same is true for rings 20 and 18. As such, when viewed on an x-ray monitor, three distinct rings are visible. Because the rings become smaller as they get closer to the marking tip—a user will be able to easily orient the marker in order to mark a spot on a patient.

Figure 3:
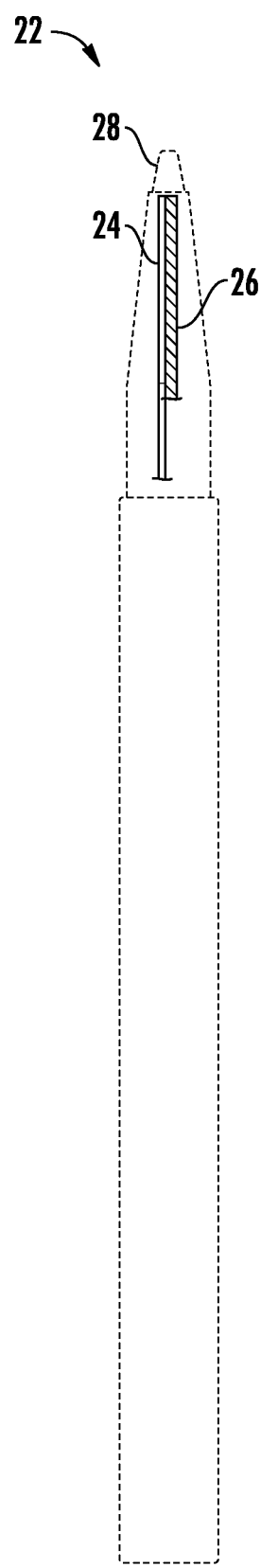
FIG. 3 shows a side view of a marker having a metallic bar disposed within the housing thereof according to an embodiment of the invention.

In another embodiment of the invention a metallic bar, rod or similar elongated structure is provided either on or within a marker. For example, FIG. 3 shows a schematic, transparent view of a marker having a metallic rod disposed therein. As shown, a metallic rod 24 (shown truncated) is provided in the interior of the marker casing. Metallic rod 24 runs substantially parallel to the longitudinal axis of marker 22. In an embodiment of the invention, rod 24 may be mounted to the cartridge 26 (shown truncated) or similar insert that holds marking material. It will be understood by one of ordinary skill in the art that metallic rod 24 may be mounted in any of various areas within the inner casing of the marker. For example, rod 24 may be mounted to the inner wall of the casing or it may be embedded therein. Alternatively, rod 24 may be mounted to the outer wall of the marker. Preferably, rod 24 is positioned to be in close proximity to the marking tip 28. In another embodiment of the invention, the outside surface of the ink cartridge 26 (or a portion thereof) is made of metallic material or surrounded by a metallic substance.

Figure 4:
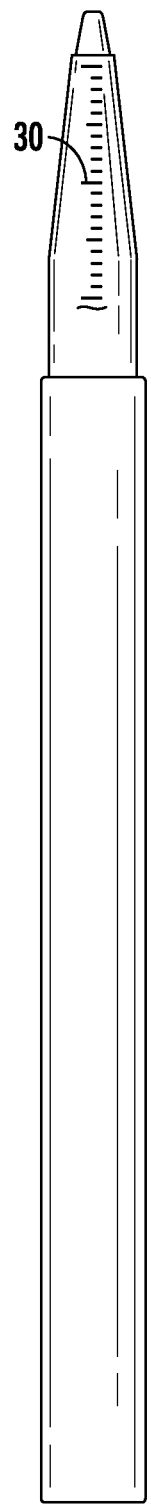
FIG. 4 shows a side view of a marker having radio-opaque material printed on the outside surface of the housing thereof according to an embodiment of the invention.

In another embodiment of the invention, the outside surface of a marker is printed with radio-opaque ink. For example, FIG. 4 shows a side view of a marker having a strip 30 of radio-opaque material printed thereon. The radio opaque strip 30 shows up on an x-ray image and it allows a doctor to identify an area of interest and mark the same—as described above. Radio-opaque strip 30 may extend over only a segment of the marker (e.g. a lower section as shown), or it may extend across the entire length of the marker housing. In one embodiment, radio-opaque strip 30 is formed of a series of tape measure lines or ruler lines. As such, a marker having such radio-opaque printed indicia may function as, both, a marker and a ruler.

It will be understood that the metallic material (either a rod, rings, or strip of radio-opaque printing—any of which cause a "visible indication" to appear on an x-ray screen) has an elongated aspect and is positioned in close proximity to the marker tip. Alternatively, the metallic material having an elongated aspect abuts or is continuous with the marker tip. As such, in use, when a clinician views the visible strip on the x-ray monitor—he/she will know that the marking material is located close to or contiguous with the lower aspect thereof.

It will be further understood that any of various radiopaque or radiodense materials or combinations thereof may be provided on or formed with the marker to cause a "visible indication" to appear on an x-ray screen according to different embodiments of the invention. For example, the rod, rings or strip of radiopaque printing may be formed of or provided with barium, iodine, or any of various radiopaque polymer formulations. The term "radiopaque" refers to any material or combinations of materials that is able to obstruct a sufficient amount of radiation so as to allow a "visible indication" to appear on an x-ray screen using an x-ray source that is conventionally used for interventional procedures known in the art. It will be further understood that the marker housing (and other parts thereof) are formed of radiolucent materials. "Radiolucent materials" refer to any of various materials or combinations thereof that allow the passage of radiation from an x-ray source conventionally used in interventional procedures known in the art, such that radiolucent material is not visible or only minimally visible on an x-ray screen. To the extent that radiolucent materials may be minimally detectable on an x-ray screen—the full boundaries of the material will not be discernable and the radiopaque material will appear significantly darker than the radiolucent material.

Figure 5:
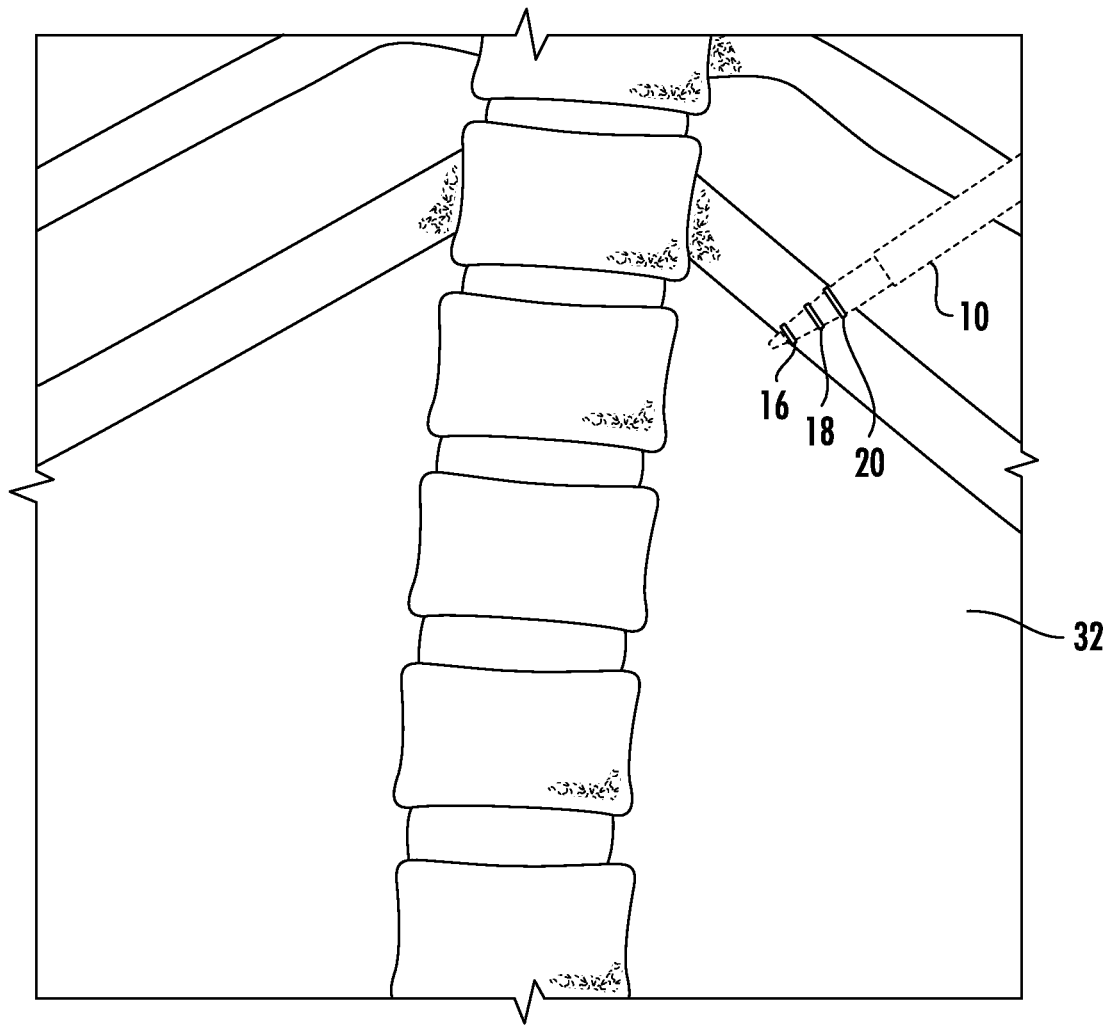
FIG. 5 shows a schematic view of an x-ray field where the rings around the marker of FIG. 1 are visible in the x-ray field according to an embodiment of the invention.

For example, FIG. 5 shows a marking device of FIG. 2 deployed in an x-ray field 32. Marker 10 is shown being held above an anatomical area displayed on an x-ray screen. Rings 16, 18, 20 of marker 10 are visible in the field (the rest of the marker in not visible on the x-ray monitor, and it is shown in dashed lines for purposes of illustration only). In use, a doctor or clinician may introduce the marker into an x-ray field and visualize the strip or similar metallic element having an elongated aspect. The doctor then watches the visible strip on the x-ray monitor and moves the marker in an area outside of the patient's body relative to an internal body area shown on the x-ray screen until an insertion or puncture area is located. Once the anatomical area of interest is selected—the user need only press the marking tip to the patient's skin to transfer ink to the same. That is, because the marking tip is disposed at the distal end of the metallic material having an elongated aspect—it is positioned for easy marking once an area of interest is located.

In all embodiments, the inventive marking device is made of plastic or such similar inexpensive material. The marker is, thus, inexpensive and disposable, and it may be included in a surgical package for single use.

In an embodiment of the invention, an inventive marker has a retractable marking tip. For example, a metallic strip, series of rings, radio-opaque printing or any such similar metallic material having an elongated aspect is provided on a marker having a spring-loaded ink cartridge which retracts and extends outside a protective housing. In use, a clinician may place the marker into the x-ray field with the ink retracted in the housing and then deploy the marking tip just prior to marking a puncture site.

In another embodiment of the invention, the inventive marker is provided with a extendable structure that allows a clinician to increase the length of the marker in order to allow an operator to remain at a safe distance from the x-ray source. For example, a marker may be provided with a telescoping barrel or it may be formed with or mounted on a foldable or collapsible structure. In use, a clinician may extend the length of the marker and insert the marking end into the x-ray field while being able to control the position of the marker from outside the x-ray field, thereby minimizing exposure to radiation.

Having described this invention with regard to specific embodiments, it is to be understood that the description is not meant as a limitation since further modifications and variations may be apparent or may suggest themselves to those skilled in the art. It is intended that the present application cover all such modifications and variations.

What is claimed is:

1. A marking device, comprising:
   a housing having an outer surface and an interior chamber;
   a cartridge containing marking material disposed in the interior chamber of the housing;
   a marking tip extending from the cartridge;
   an elongated structure comprising radiopaque material having a first end and a second end disposed within the interior chamber;
   the first end of the elongated structure comprising radiopaque material disposed in proximity to the marking tip;
   whereby the radiopaque material comprises material that at least partially obstructs the passage of radiant energy and is visible in an x-ray field.

2. The marking device of claim 1, whereby the elongated structure comprising radiopaque material comprises a metallic rod disposed in the interior chamber of the housing.

3. The marking device of claim 1, whereby the housing is formed of material that does not obstruct the passage of radiant energy.

4. The marking device of claim 3, whereby the housing is formed of plastic.

5. The marking device of claim 1, whereby the cartridge comprises material that is absorptive to the marking material.

6. The marking device of claim 1, whereby the marking tip is formed of porous fibrous material.

7. A marking device, comprising:
   a housing having an outer surface and an interior chamber;
   a cartridge containing marking material disposed in the interior chamber of the housing;
   a marking tip extending from the cartridge;
   a segment of radiopaque material having an elongated aspect defined by a first end and a second end, the segment of radiopaque material having an elongated aspect disposed outside of the cartridge and oriented substantially parallel to a longitudinal axis of the marking device;
   the first end of the segment of radiopaque material disposed in proximity to the marking tip;
   whereby the radiopaque material is formed of a material that at least partially obstructs the passage of radiant energy and is visible in an x-ray field.

8. The marking device of claim 7, whereby the segment of radiopaque material having an elongated aspect defined by a first end and a second end comprises a plurality of metallic rings.

9. The marking device of claim 8, whereby the plurality of rings are attached to the outer surface of the housing.

10. The marking device of claim 8, whereby the plurality of rings is attached to a sloping area on the marking device.

11. A marking device, comprising:
    a housing having an outer surface and an interior chamber, the housing formed of radiolucent material;
    a cartridge having an outer surface and an interior containing marking material disposed in the interior chamber of the housing;
    a marking tip extending from the cartridge;
    a segment of radiopaque material having an elongated aspect disposed on the outer surface of the cartridge, the segment of radiopaque material having a first end and a second end;
    the first end of the radiopaque material disposed in proximity to the marking tip;
    whereby the radiopaque material is configured to form a visible indication on an x-ray screen when the marking device is introduced into an x-ray field.

* * * * *